United States Patent
Lee et al.

(10) Patent No.: US 10,980,964 B2
(45) Date of Patent: Apr. 20, 2021

(54) MASK-TYPE NASAL CANNULA

(71) Applicant: SOGANG UNIVERSITY RESEARCH FOUNDATION, Seoul (KR)

(72) Inventors: Tae-Soo Lee, Gyeonggi-do (KR); Seung Kwon Oh, Namyangju-si (KR); Seung Hyun Ryu, Seoul (KR); Bong Kwan Son, Busan (KR); Sung Hun Ha, Seoul (KR); Dong Min Shin, Seoul (KR); Yong Sang Shin, Seoul (KR)

(73) Assignee: Sogang University Research Foundation, Seoul (KR)

( * ) Notice: Subject to any disclaimer, the term of this patent is extended or adjusted under 35 U.S.C. 154(b) by 263 days.

(21) Appl. No.: 16/308,317

(22) PCT Filed: Aug. 4, 2016

(86) PCT No.: PCT/KR2016/008619
§ 371 (c)(1),
(2) Date: Dec. 7, 2018

(87) PCT Pub. No.: WO2017/213297
PCT Pub. Date: Dec. 14, 2017

(65) Prior Publication Data
US 2019/0262570 A1    Aug. 29, 2019

(30) Foreign Application Priority Data

Jun. 10, 2016  (KR) ........................ 10-2016-0072630

(51) Int. Cl.
*A61M 16/06*   (2006.01)
*A41D 13/11*   (2006.01)
*A61M 16/20*   (2006.01)

(52) U.S. Cl.
CPC ......... *A61M 16/0683* (2013.01); *A41D 13/11* (2013.01); *A61M 16/06* (2013.01);
(Continued)

(58) Field of Classification Search
CPC .............. A61M 16/06; A61M 16/0666; A61M 16/0672; A61M 16/0683; A61M 16/208; A41D 13/11
See application file for complete search history.

(56) References Cited

U.S. PATENT DOCUMENTS 3,403,677 A * 10/1968 Struve .................. A61M 16/06
                                                       128/206.28
6,968,844 B2    11/2005 Liland et al.
(Continued)

FOREIGN PATENT DOCUMENTS

CN    102762249 A    10/2012
CN    105283212 A    1/2016
(Continued)

*Primary Examiner* — Kathryn E Ditmer
(74) *Attorney, Agent, or Firm* — Rabin & Berdo, P.C.

(57) ABSTRACT

A nasal cannula according to an embodiment of the present invention includes: an oxygen supplying portion which forms a space inside in which a nose and a mouth of a user can be disposed and is able to supply oxygen in a state of being put on by the user into the nose of the user; and a mask portion to which the oxygen supplying portion is attached in a detachable manner therein and is configured to be put on a face of the user. Since a space in which a nose and a mouth of a user can be disposed is provided inside the oxygen supplying portion so that a user can put on the nasal cannula in a convenient state and the oxygen supplying portion is put on in a state of being supported by the mask portion, oxygen can be supplied into the nose of the user and at the same time external air can be filtered.

9 Claims, 8 Drawing Sheets

(52) U.S. Cl.
CPC ........ *A61M 16/0672* (2014.02); *A61M 16/20* (2013.01); *A61M 16/208* (2013.01)

(56) References Cited

U.S. PATENT DOCUMENTS

| | | |
|---|---|---|
| 7,255,107 B1 | 8/2007 | Gomez |
| 9,138,169 B2 | 9/2015 | Beard |
| 2008/0060654 A1* | 3/2008 | Vandine ............ A61M 16/0683 128/207.11 |
| 2010/0122699 A1 | 5/2010 | Birnkrant |
| 2011/0203591 A1* | 8/2011 | Amarasinghe ...... A61M 16/065 128/205.25 |
| 2012/0305001 A1* | 12/2012 | Tatkov ............... A61M 16/0622 128/205.25 |
| 2013/0104902 A1 | 5/2013 | Ho et al. |
| 2016/0030695 A1 | 2/2016 | Chang |
| 2018/0264220 A1* | 9/2018 | Hurt .................. A61M 16/0605 |

FOREIGN PATENT DOCUMENTS

| | | |
|---|---|---|
| KR | 20-0204653 Y1 | 12/2000 |
| KR | 10-2006-0064849 A | 6/2006 |
| KR | 10-2014-0078653 A | 6/2014 |

* cited by examiner (a)

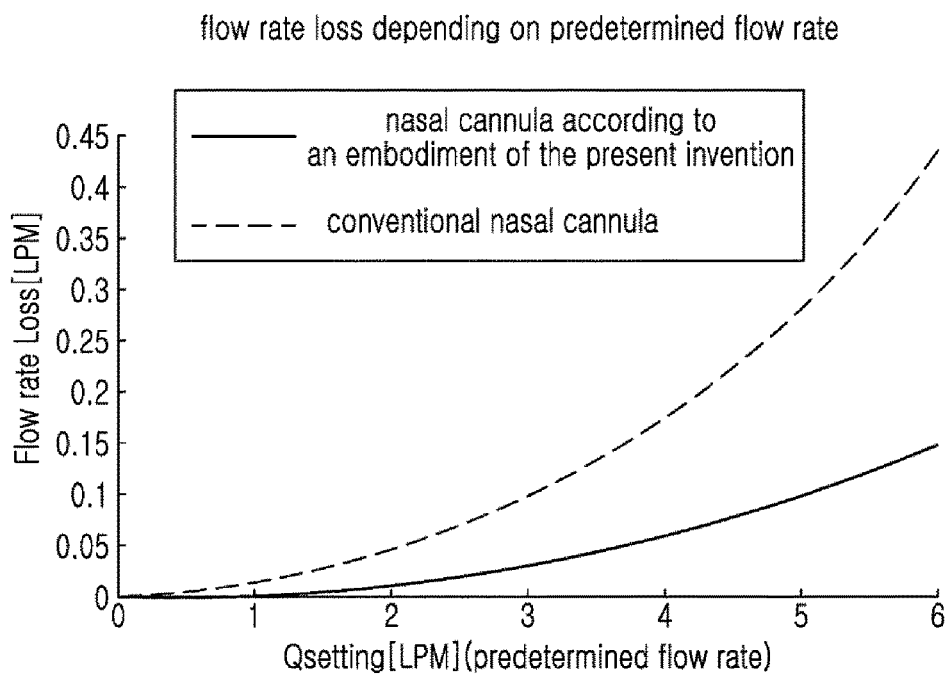

| | nasal cannula according to an embodiment of the present invention | conventional nasal cannula |
|---|---|---|
| flow rate loss at predetermined 1 LPM [LPM] | 0.0037 | 0.0084 |
| flow rate loss at predetermined 2 LPM [LPM] | 0.0174 | 0.0366 |
| flow rate loss at predetermined 3 LPM [LPM] | 0.0447 | 0.0887 |
| flow rate loss at predetermined 4 LPM [LPM] | 0.0889 | 0.1680 |
| flow rate loss at predetermined 5 LPM [LPM] | 0.1527 | 0.2773 |
| flow rate loss at predetermined 6 LPM [LPM] | 0.2389 | 0.4185 |

*discharge pressure 0.6bar, on the experiment with 99.9% oxygen

MASK-TYPE NASAL CANNULA

TECHNICAL FIELD

The present invention relates to a nasal cannula having an oxygen supplying portion of a supporting frame shape for supplying oxygen into a nose and a mask portion to/from which the oxygen supplying portion can be attached/detached.

BACKGROUND ART

Generally chronic obstructive pulmonary disease patients use a breathing assisting device supplying oxygen because of decrease in breathing capacity due to damages on an airway and a lung.

An oxygen nasal cannula is a representative breathing assisting device.

An oxygen nasal cannula is provided with a nosepiece which is branched into two parts to form a prong and a tube for supplying oxygen into the nosepiece.

The oxygen nasal cannula is put on to a patient by inserting the prong of the nosepiece into patient's nostrils and then hanging the tube which is extended from the nosepiece onto patient's ear to fix just like wearing eyeglasses.

Meanwhile, when the particulate matter concentration becomes higher, toxic substances including the particulate matters may cause inflammatory responses in the lung to aggravate chronic obstructive pulmonary disease. Accordingly, the chronic obstructive pulmonary disease patients wears the particulate matter mask on the oxygen nasal cannula to slightly prevent the inflammatory responses by the toxic substances including the particulate matters.

However, when the particulate matter mask is put on the oxygen nasal cannula, a gap between the particulate matter mask and the patient's face because of a tube which is elongated from the nose of the patient to the rear side of the ear so that the mask dose not tightly contact the patient's face, and thus there is a problem in that the particulate matters may flow into the respiratory system through the gap without being filtered.

Further, when the particulate matter mask is put on the oxygen nasal cannula, the strap of the mask pressures the patient's ear together with the tube which is hung on the patient's ear to cause inconveniences to the patient, and this may cause decubitus ulcer. Furthermore, because of these problems, it is difficult for the patient to put on the mask for a long time even in a situation of high concentration of particulate matters.

DETAILED DESCRIPTION OF THE INVENTION

Technical Problem

The present invention has been made in an effort to solve the above-mentioned problems and provides a nasal cannula which can tightly adhere to the face of the patient when it is coupled with the particulate matter mask to minimize the inflow of external air and allows a long time wearing without bad effects on the body of the patient.

Technical Solution

A nasal cannula according to an embodiment of the present invention includes: an oxygen supplying portion which forms a space inside in which a nose and a mouth of a user can be disposed and is able to supply oxygen in a state of being put on by the user into the nose of the user; and a mask portion to which the oxygen supplying portion is attached in a detachable manner therein and is configured to be put on a face of the user.

The oxygen supplying portion may include: a frame portion which is formed in a dome structure so as to form the space inside, a flow passage allowing oxygen supplied from outside to flow being formed in a single structure therein; and a prong portion which is coupled to the frame portion to be disposed in the space in a state of being communicated with the flow passage and being inserted into the nose of the user in a state of being put on by the user.

The frame portion may include: a plurality of horizontal supporting members which are formed in an arch structure and are disposed in a predetermined direction; and a plurality of vertical supporting members which are formed in an arch structure and are disposed along an outer contour of the horizontal supporting members to intersect the horizontal supporting members.

The vertical supporting member may include: a main supporting member which forms the flow passage thereinside, a first coupling nozzle which is protruded into the space to be coupled to the prong portion being formed at one side of the main supporting member, and a second coupling nozzle which is outwardly protruded to penetrate the mask portion being formed at the other side of the main supporting member; and auxiliary supporting members which are disposed at both sides of the main supporting member along an outer contour of the horizontal supporting member.

The frame portion may further include: a nose supporting member which is bent and extended in a predetermined direction from an edge portion of the horizontal supporting member which is disposed at one end of the vertical supporting member and is provided with an indentation portion at an inner interior center portion thereof in which a nose of the user can be seated; and a thin supporting member which is bent and extended in a predetermined direction from an edge portion of the horizontal supporting member which is disposed at the other end of the vertical supporting member and contacts a chin of the user when the user puts on the nasal cannula.

The prong portion may include: a coupling portion which is coupled to the first coupling nozzle; a bifurcated discharging portion which is bifurcated to be inserted into a nose of the user and discharges oxygen when the oxygen is supplied; and a position regulation portion which is interposed between the coupling portion and the bifurcated discharging portion to connect the coupling portion and the bifurcated discharging portion and is made of flexible material so as to regulate the position and the angle of the bifurcated discharging portion within the space.

The mask portion may include: a main body which encloses a face of the user and is provided with bands at both sides thereof which are configured to be hung on ears of the user; and a supporting member which is provided at a lower side of the main body and in which a through hole corresponding to an outer surface of the second coupling nozzle is formed so as to be coupled with the second coupling nozzle.

The oxygen supplying portion may further include a connector which is coupled to the frame portion and transmits oxygen supplied from an external device to the flow passage. The connector may include: a connecting portion which is coupled to the supporting portion and is coupled to one side of the second coupling nozzle which is protruded to the outside of the supporting portion; and a connecting tube which connects the external device and the connecting portion together and is configured to allow oxygen to flow therethrough.

An outer surface of the second coupling nozzle and an inner surface of the supporting portion in which the through hole is formed may be formed in a tapered shape, and an inner surface of the connecting portion may be formed in a shape corresponding to the outer surface of the second coupling nozzle.

The supporting portion may include: a first supporting member of a plate shape which is connected to the main body; and a second supporting member which is inclinedly protruded from the first supporting member with a predetermined angle to penetrate the main body and is formed in a tapered shape.

The supporting portion may include: a valve frame which is connected to the main body and defines a flow passage therein; a valve cap which is coupled to a front side of the valve frame and is provided with a plurality of discharging holes disposed along a circumference thereof; and a valvular member which is disposed between the valve frame and the valve cap and opens/closes the flow passage depending on breathing of the user.

Advantageous Effects

According to the present invention, since a space in which a nose and a mouth of a user can be disposed is provided inside the oxygen supplying portion so that a user can put on the nasal cannula in a convenient state and the oxygen supplying portion is put on in a state of being supported by the mask portion, oxygen can be supplied into the nose of the user and at the same time external air can be filtered.

Further, since an interference between the oxygen supplying portion and the mask portion is eliminated, a long time wearing is possible and the mask portion can tightly contact the face of the user so as to minimize the inflow of the external air and to completely filter the external air.

Further, since the flow passage at the interior center of the frame portion which communicates with the prong portion is formed in a single structure, the fluidal resistance can be substantially reduced compared to the conventional nasal cannula so as to minimize the flow rate loss and thereby it is possible to supply the amount of oxygen closely similar to the predetermined amount of flow and to minimize the energy consumption.

BRIEF DESCRIPTION OF THE DRAWINGS

FIG. 1 shows a state that a nasal cannula according to an embodiment of the present invention is put on.

FIG. 8 shows experimental results of flow rate loss per unit flow rate of a nasal cannula according to an embodiment of the present invention and a conventional nasal cannula.

DETAILED DESCRIPTION OF THE EMBODIMENTS

Embodiments of the present invention will be described referring to the accompanying drawings hereinafter.

Figure 1:
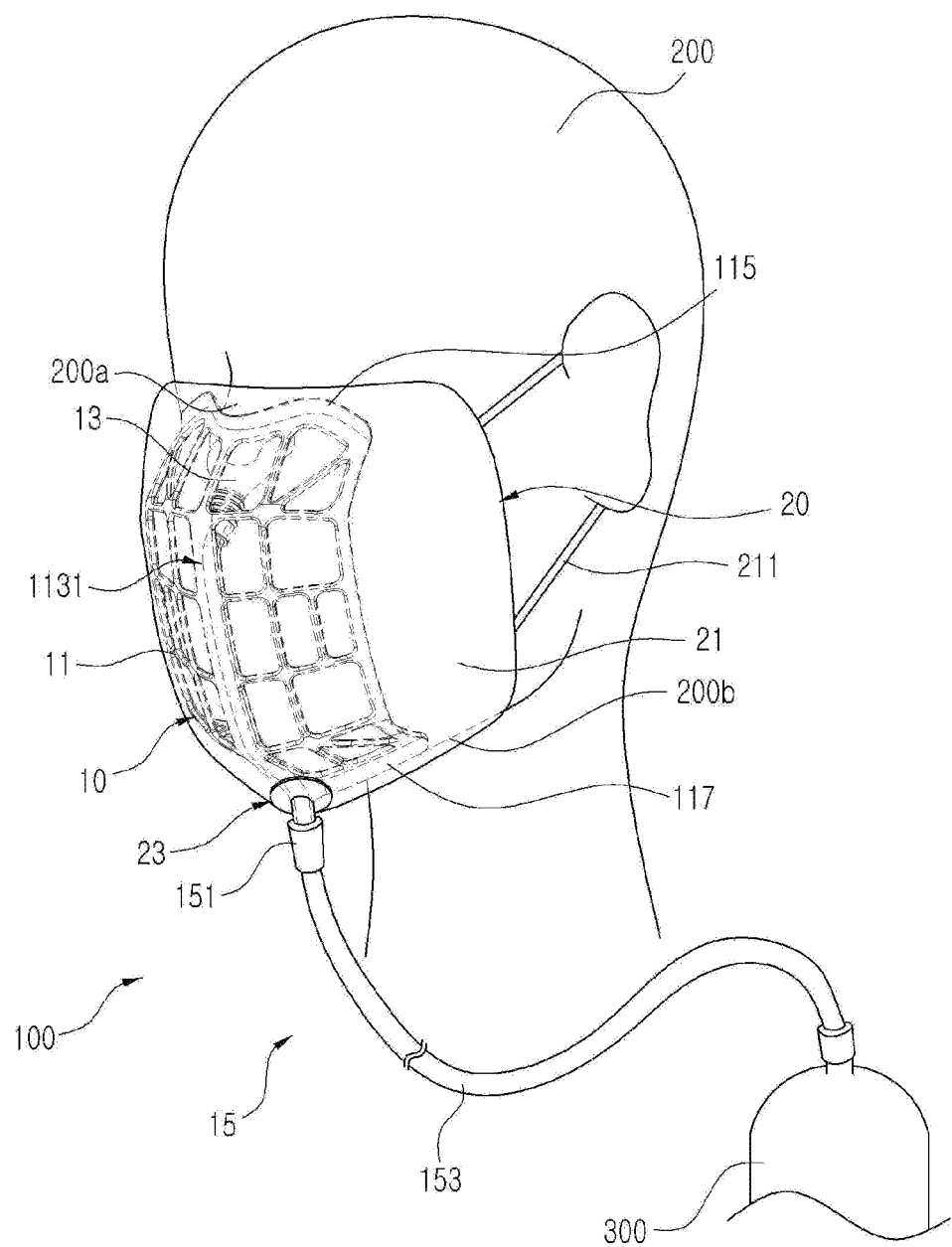

Referring to FIG. 1, a nasal cannula 100 according to an embodiment of the present invention includes an oxygen supplying portion 10.

The oxygen supplying portion 10 forms a space 11a therein in which a nose 200a and a mouth of a patient may be disposed, and is formed in a type of a supporting frame which is able to supply oxygen into the nose 200a of a user 200 who puts on the same.

In more detail, the oxygen supplying portion 10 may include a frame portion 11 which defines the space 11a and a prong portion 13 which supplies oxygen into the nose 200a of the user 200.

Figure 2:
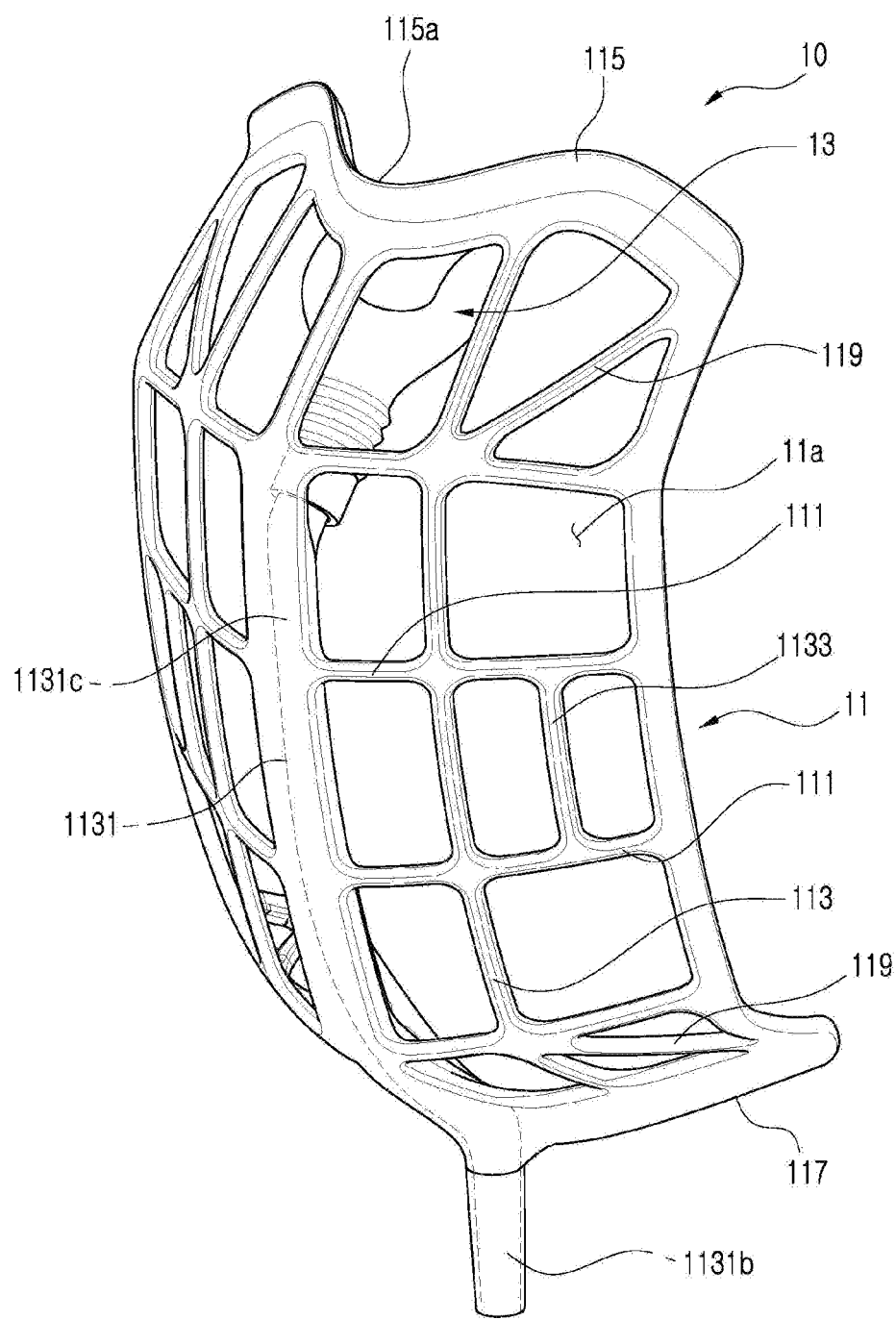
FIG. 2 is a front perspective view of a cannula portion of a nasal cannula according to an embodiment of the present invention.
Figure 3:
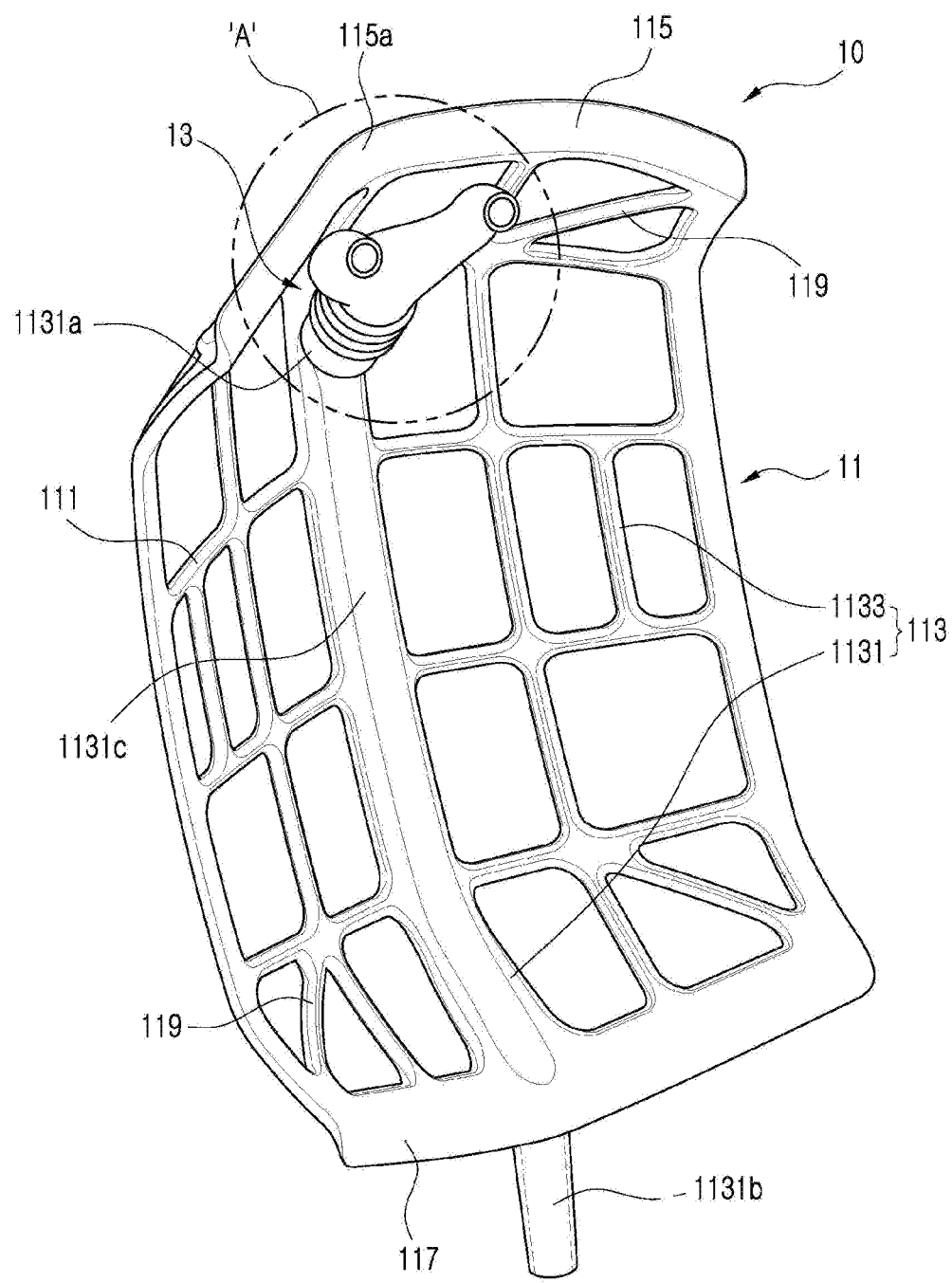
FIG. 3 is a rear perspective view of a cannula portion of a nasal cannula according to an embodiment of the present invention.

Referring to FIG. 2 and FIG. 3, the frame portion 11 is formed in a dome structure to define the space 11a therein in which the nose 200a and the mouth of the user 200 are disposed, and a flow passage 1131c through which oxygen flows from the outside may be formed therein.

In more detail, the frame portion 11 may include a plurality of horizontal supporting members 111 which are respectively formed in an arch shape and are disposed in a predetermined direction and a plurality of vertical supporting members 113 which are respectively formed in an arch shape and are disposed along the outer contour of the horizontal supporting members 111 to intersect the horizontal supporting member 111. That is, both the horizontal supporting members 111 and the vertical supporting members 113 are formed in an arch shape and are disposed to intersect one another an outer contours thereof to form a dome structure. For example, the arch structure described here does not mean a complete arc shape but may mean a curved structure toward the outside to form the space 111a therein. Also, the dome structure does not mean a complete hemisphere but may mean a structure such as a bowl which is formed by the arch structure which is described in the former.

Here, the vertical supporting member 113 may include a main supporting member 1131 and an auxiliary supporting member 1133.

The main supporting member 1131 forms a flow passage 1131c in a single structure, and d a first coupling nozzle 1131a which is protruded into the space 11a and is coupled to the prong portion 13 is formed at one side thereof and a second coupling nozzle 1131b which is protruded toward the outside and penetrates a mask portion 20 is formed at the other side thereof. The auxiliary supporting member 1133 is formed to have a thickness less than the main supporting member 1131 and may be disposed at both sides of the main supporting member 1131 along the outer contour of the horizontal supporting member 111.

At this time, the single structure means a structure of being independently formed in an interior center of the frame portion 111 so as to supply oxygen in a predetermined flow rate to the prong portion 13, as shown in FIG. 3.

Referring to FIG. 8, in the conventional nasal cannula, a nosepiece connected to a main tube is designed to be bifurcated to cause a fluidal resistance to be substantially increased.

However, in the nasal cannula 100, the flow passage 1131c connected to the prong portion 13 is formed in a single structure in the interior center of the frame portion 11, so that a fluidal resistance can be substantially reduced compared to the conventional nasal cannula. That is, as shown in FIG. 8, when oxygen is supplied to the nasal cannula 100, a loss in a flow rate can be minimized compared to the conventional nasal cannula. Accordingly, the amount of oxygen supplied by the nasal cannula could be closely similar to the predetermined amount, and thus the energy consumption can be minimized.

As an example, the value of the flow rate loss can be obtained from a difference between the predetermined flow rate from the external device supplying oxygen and the flow rate which can be actually obtained when the nasal cannula is connected to the external device.

The frame portion 11 may further include a nose supporting member 115, a chin supporting member 117 and an edge connection supporting member 119.

The nose supporting member 115 may be bent and extended in a predetermined direction from an edge portion of the horizontal supporting member 111 which is disposed at one end of the vertical supporting member 113. In addition, the nose supporting member 115 may be provided with an indentation portion 115a at an interior center portion thereof in which a nose 200a of the user 200 can be seated. Accordingly, as shown in FIG. 1, when the user 200 puts on the nasal cannula, the nose supporting member 115 contacts the nose 200a of the user 100.

The chin supporting member 117 may be bent and extended in a predetermined direction from an edge portion of the horizontal supporting member 111 which is disposed at the other end of the vertical supporting member 113. Accordingly, as shown in FIG. 1, when the user 200 puts on the nasal cannula, the chin supporting member 117 contacts the chin 200b of the user 200.

The edge connection supporting member 119 connects the edges of the lattice which is formed by the vertical supporting member 113 and the horizontal supporting member 111. That is, the edge connection supporting member 119 connects the outermost edge which has a poor structural strength to the edge of the inner lattice so as to maintain the frame portion 111 in a more solid state.

Figure 4:
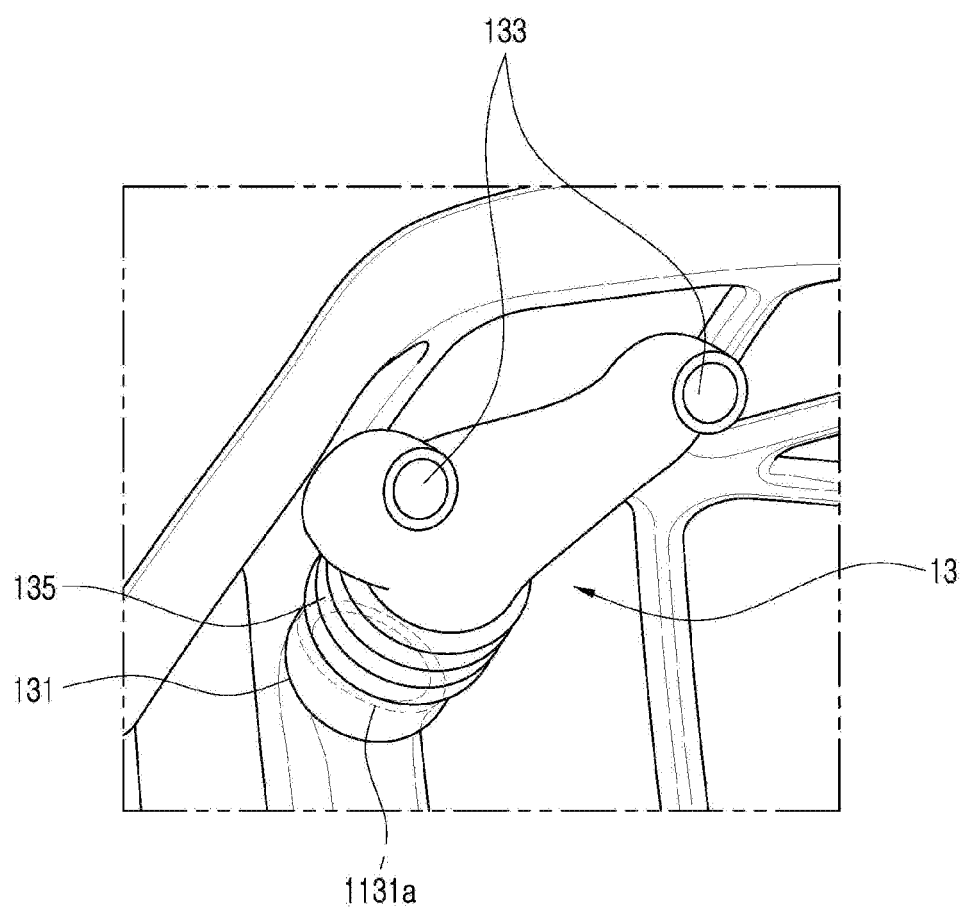
FIG. 4 is an enlarged view of 'A' portion in FIG. 3.

Referring to FIG. 1 and FIG. 4, the prong portion 13 is coupled to the frame portion 11 in a state of being communicated with the flow passage 1131c and is disposed to the space 11a, and is inserted into the nose 200a when the user 200 puts on the nasal cannula.

In more detail, the prong portion 13 may include a coupling portion 131 which is coupled to the first coupling nozzle 1131a, a bifurcated discharging portion 133 which is bifurcated and is inserted into the nose 200a and discharges oxygen when oxygen is supplied, and a position regulation portion 135 which is interposed between the coupling portion 131 and the bifurcated discharging portion 133 to connect the coupling portion 131 and the bifurcated discharging portion 133 and is made of flexible material so as to regulate the position and the angle of the bifurcated discharging portion 133 within the space 11a. For example, the position regulation portion 135 may be formed by bellows type tube.

In addition, the oxygen supplying portion 10 may further include a connector 15 which is coupled to the frame portion 11 and transfers oxygen supplied from the external device 300 to the flow passage 1131c.

Referring to FIG. 1, the connector 15 may include a connecting portion 151 which is coupled to the supporting portion 23 to be coupled to one end of the second coupling nozzle 1131b which is outwardly protruded from supporting portion 23, and a connecting tube 153 which connects the external device 300 and the connecting portion 151 together and is configured to allow oxygen to flow therethrough.

Meanwhile, the nasal cannula 100 includes the mask portion 20.

Figure 5:
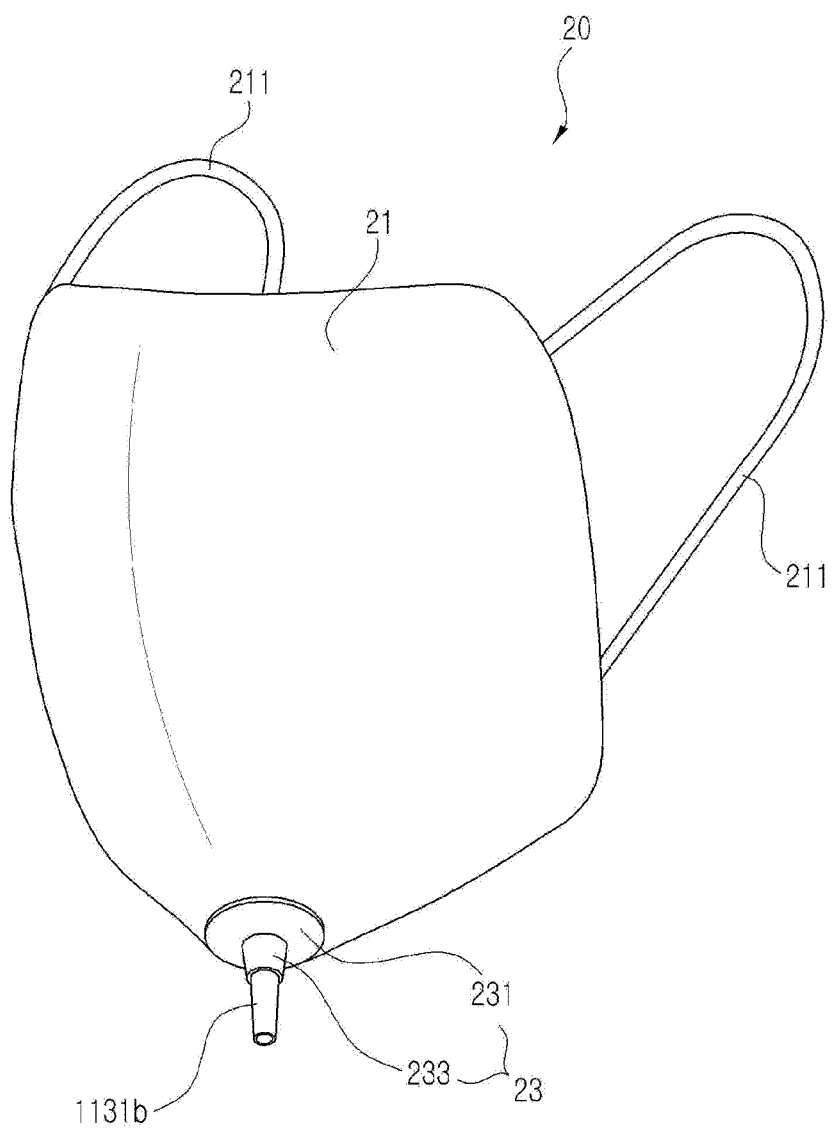
FIG. 5 shows a mask portion of a nasal cannula according to an embodiment of the present invention.

Referring to FIG. 5, the mask portion 20 is configured to allow the oxygen supplying portion 10 to be attached in a detachable manner and to be put on the face of the user 200.

The mask portion 20 may include a main body 21.

The main body 21 may enclose the face of the user 200 and may be provided with bands 211 at both sides thereof which are configured to be hung on the ears of the user 200.

In addition, the mask portion 20 may include the supporting portion 23 which is provided at the lower side of the main body 21 and in which a through hole 23a corresponding to the outer surface of the second coupling nozzle 1131b is formed so as to be coupled with the second coupling nozzle 1131b.

Figure 6:
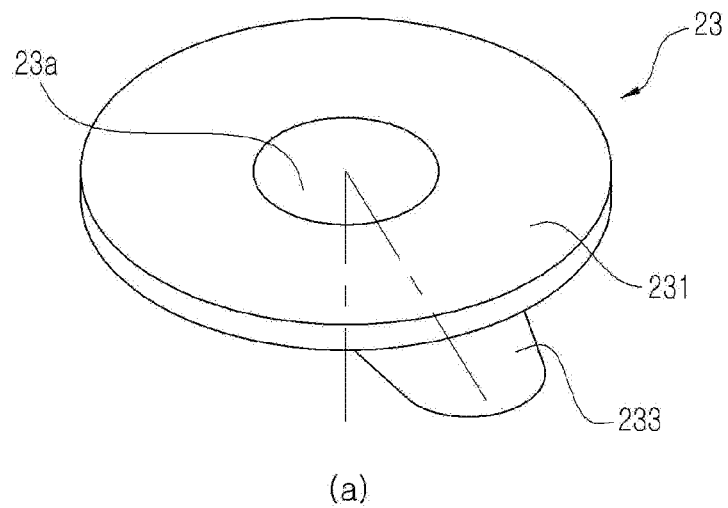
FIG. 6 schematically shows an exemplary embodiment of a supporting portion provided to a mask portion of a nasal cannula according to an embodiment of the present invention and a state that a second coupling nozzle and a connecting portion are coupled to the supporting portion.
Figure 6:
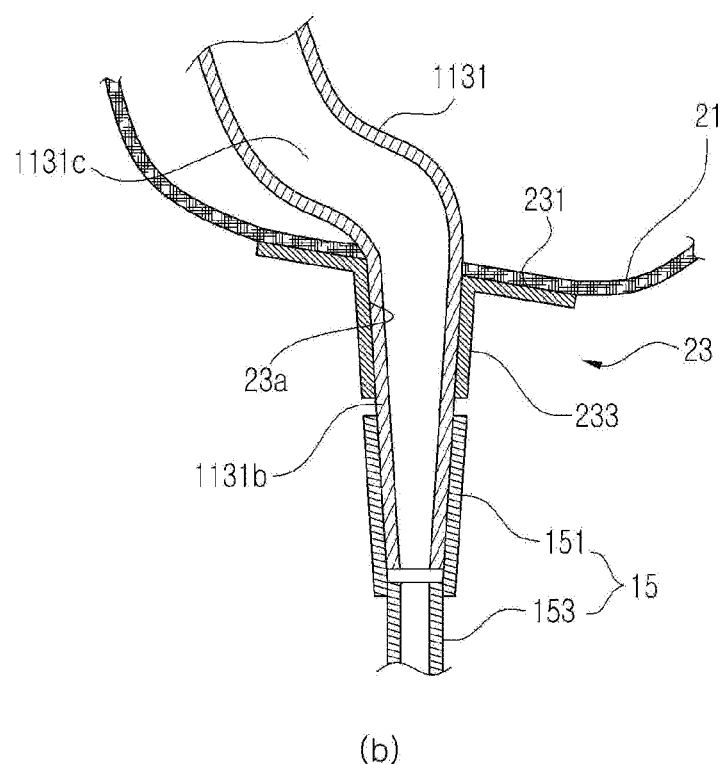

Here, the outer surface of the second coupling nozzle 1131b and the inner surface of the supporting portion 23 defining the through hole 23a, as shown in FIG. 6, may be formed in a tapered shape, and the inner surface of the connecting portion 151 may be formed in a shape corresponding to the outer surface of the second coupling nozzle 1131b. Accordingly, when the user wears the nasal cannula 100, the tensile force of the band 211 which is connected to the main body 21 of the mask portion 20 pulls the main body 21 so as to adhere the oxygen supplying portion 10 toward the face of the user, so that the inner surface of the supporting portion 23 provided to the main body 21 tightly contact the outer surface of the second coupling nozzle 1131b of the oxygen supplying portion 10 to prevent external air from inflowing through a gap between the outer surface of the second coupling nozzle 1131b and the inner surface of the supporting portion 23. In addition, the connecting portion 151 can tightly contact to the outer surface of the second coupling nozzle 1131b via the tapered inner surface thereof.

The supporting portion 23 is connected to the main body 21 and is configured to have a shape to be able to support the second coupling nozzle 1131b.

In more detail, the supporting portion 23 may include a first supporting member 231 which is connected to the main body 21 and has a plate shape, and a second supporting member 233 which is inclinedly protruded from the first supporting member 231 with a predetermined angle to penetrate the main body 21 and is formed in a tapered shape. For example, the first supporting member 231 and the second supporting member 233 may be formed in a separable structure or in an integral structure.

The supporting portion 23 may be formed in a valve structure.

Figure 7:
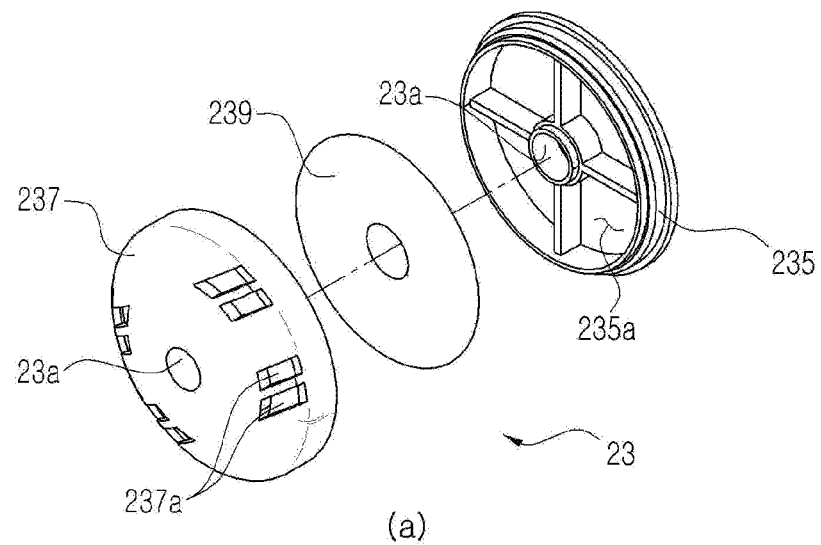
FIG. 7 schematically shows another exemplary embodiment of a supporting portion provided to a mask portion of a nasal cannula according to an embodiment of the present invention and a state that a second coupling nozzle and a connecting portion are coupled to the supporting portion.
Figure 7:
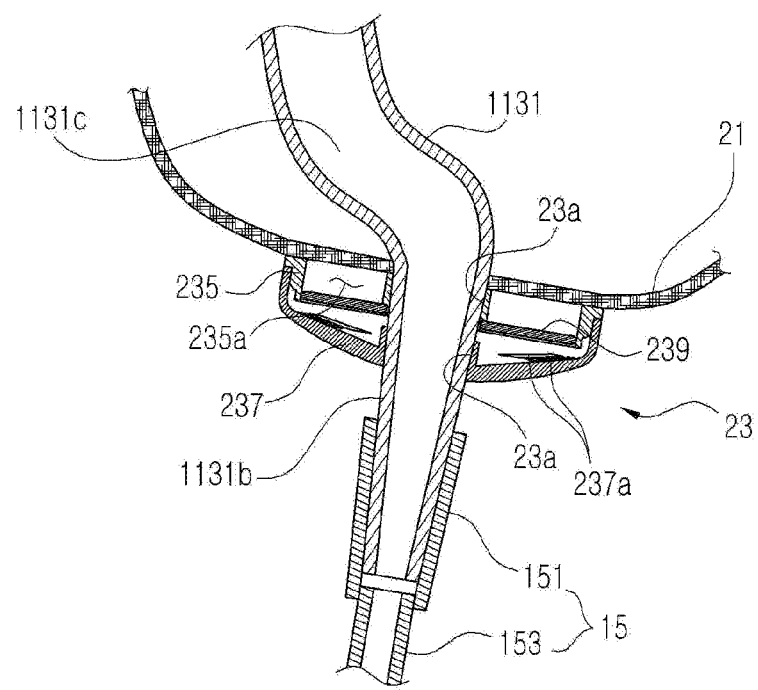

Referring to FIG. 7, the supporting portion 23 may include a valve frame 235 which is connected to the main body 21 and defines a flow passage 235a therein, a valve cap 237 which is coupled to a front side of the valve frame 235 and is provided with a plurality of discharging holes 237a disposed along a circumference thereof, and a valvular member 239 which is disposed between the valve frame 235 and the valve cap 237 and opens/closes the flow passage depending on the breathing of the user.

That is, if the user 200 exhales in a state that the flow passage 235*a* is closed, the air discharged from the user 200 passes through the main body 21 of the mask portion 20 and inflows into the flow passage 235*a* formed in the valve frame 235 to press the valvular member 239, and accordingly the valvular member 239 moves forward to open the flow passage 235*a* so that the air can be discharged to the outside through the plurality of the discharging holes 237*a*.

As such, according to the present invention, since the space 11*a* in which the nose 200*a* and the mouth of the user 200 may be disposed is formed inside the oxygen supplying portion 10, the user 200 can wear the nasal cannula in a convenient state and since the oxygen supplying portion 10 is put on in a state of being supported by the mask portion 20, oxygen can be supplied into the nose 200*a* and at the same time the external air can be filtered.

Further, the interference between the oxygen supplying portion 10 and the mask portion 20 is removed, a long time wearing is possible and also the mask portion 20 can tightly contact the face of the user 200 so that the inflowing of the external air can be minimized and the external air can be completely filtered.

Further, since the flow passage 1131*c* communicating with the prong portion 13 is formed in a single structure in the interior center of the frame portion 11, the fluidal resistance can be substantially reduced compared to the conventional nasal cannula so as to minimize the flow rate loss, and thereby the amount of oxygen supplied to the user 200 by the nasal cannula could be closely similar to the predetermined amount and the energy consumption can be minimized.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

INDUSTRIAL APPLICABILITY

The nasal cannula according to an embodiment of the present invention can be used as a breathing assisting device for chronic obstructive pulmonary disease patient.

The invention claimed is:

1. A nasal cannula comprising:
an oxygen supplying portion which forms a space inside in which a nose and a mouth of a user can be disposed and is able to supply oxygen in a state of being put on by the user into the nose of the user; and
a mask portion to which the oxygen supplying portion is attached in a detachable manner therein and is configured to be put on a face of the user;
wherein the oxygen supplying portion comprises:
a frame portion which is formed in a dome structure so as to form the space inside, a flow passage allowing oxygen supplied from outside to flow being formed in a single structure therein; and
a prong portion which is coupled to the frame portion to be disposed in the space in a state of being communicated with the flow passage and configured to be inserted into the nose of the user in a state of being put on by the user; and
wherein the frame portion comprises:
a plurality of horizontal supporting members which are formed in an arch structure and are disposed in a predetermined direction; and
a plurality of vertical supporting members which are formed in an arch structure and are disposed along an outer contour of the horizontal supporting members to intersect the horizontal supporting members.

2. The nasal cannula of claim 1, wherein the plurality of vertical supporting member comprises:
a main supporting member which forms the flow passage thereinside, a first coupling nozzle which is protruded into the space to be coupled to the prong portion being formed at one side of the main supporting member, and a second coupling nozzle which is outwardly protruded to penetrate the mask portion being formed at another side of the main supporting member; and
auxiliary supporting members which are disposed at both lateral sides of the main supporting member.

3. The nasal cannula of claim 1, wherein the frame portion further comprises:
a nose supporting member which is bent and extended in a predetermined direction from an edge portion of a horizontal supporting member which is disposed at one end of a vertical supporting member and is provided with an indentation portion at an inner interior center portion thereof in which the nose of the user can be seated; and
a thin supporting member which is bent and extended in a predetermined direction from an edge portion of another horizontal supporting member which is disposed at another end of the vertical supporting member and configured to contacts a chin of the user when the user puts on the nasal cannula.

4. The nasal cannula of claim 2, wherein the prong portion comprises:
a coupling portion which is coupled to the first coupling nozzle;
a bifurcated discharging portion which is bifurcated to be inserted into the nose of the user and configured to discharges oxygen when the oxygen is supplied; and
a position regulation portion which is interposed between the coupling portion and the bifurcated discharging portion to connect the coupling portion and the bifurcated discharging portion and is made of flexible material so as to regulate a position and angle of the bifurcated discharging portion within the space.

5. The nasal cannula of claim 2, wherein the mask portion comprises:
a main body which is configured to encloses the face of the user and is provided with bands at both sides thereof which are configured to be hung on ears of the user; and
a supporting portion which is provided at a lower side of the main body and in which a through hole corresponding to an outer surface of the second coupling nozzle is formed so as to be coupled with the second coupling nozzle.

6. The nasal cannula of claim 5, wherein the oxygen supplying portion further comprises a connector which is coupled to the frame portion and configured to transmits oxygen supplied from an external device to the flow passage, and
wherein the connector comprises:
a connecting portion which is coupled to one side of the second coupling nozzle which is protruded to outside of the supporting portion; and
a connecting tube which is configured to connects the external device and the connecting portion together and is configured to allow oxygen to flow therethrough.

7. The nasal cannula of claim 6, wherein the outer surface of the second coupling nozzle and an inner surface of the supporting portion in which the through hole is formed are formed in a tapered shape, and wherein an inner surface of the connecting portion is formed in a shape corresponding to the outer surface of the second coupling nozzle.

8. The nasal cannula of claim 7, wherein the supporting portion comprises:
   a first supporting member of a plate shape which is connected to the main body; and
   a second supporting member which is inclinedly protruded from the first supporting member with a predetermined angle and is formed in a tapered shape.

9. The nasal cannula of claim 7, wherein the supporting portion comprises:
   a valve frame which is connected to the main body and defines a flow passage therein;
   a valve cap which is coupled to a front side of the valve frame and is provided with a plurality of discharging holes disposed along a circumference thereof; and
   a valvular member which is disposed between the valve frame and the valve cap and configured to opens/closes the flow passage depending on breathing of the user.

\* \* \* \* \*